US 12,432,003 B2

United States Patent
Duval et al.

(10) Patent No.: US 12,432,003 B2
(45) Date of Patent: Sep. 30, 2025

(54) SINGLE STREAM PROTOCOL FOR MULTIPLE SENSOR MEDICAL SYSTEM

(71) Applicant: Boston Scientific Scimed, Inc., Maple Grove, MN (US)

(72) Inventors: George Wilfred Duval, Sudbury, MA (US); Louis J. Barbato, Franklin, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/752,917

(22) Filed: Jun. 25, 2024

(65) Prior Publication Data

US 2024/0348360 A1  Oct. 17, 2024

Related U.S. Application Data

(63) Continuation of application No. 17/474,225, filed on Sep. 14, 2021, now Pat. No. 12,057,928.

(60) Provisional application No. 63/079,069, filed on Sep. 16, 2020.

(51) Int. Cl.
  *H04J 13/00* (2011.01)
  *H04B 1/707* (2011.01)

(52) U.S. Cl.
  CPC ............ *H04J 13/004* (2013.01); *H04B 1/707* (2013.01)

(58) Field of Classification Search
  CPC .... H04B 1/707; H04B 1/709; H04B 1/71635; H04B 1/71637; H04J 13/0022; H04J 13/0025; H04J 13/004
  USPC ........ 375/141, 142, 146, 147, 150; 370/335, 370/342
  See application file for complete search history.

(56) References Cited

U.S. PATENT DOCUMENTS

| | | | |
|---|---|---|---|
| 6,222,819 B1 | 4/2001 | Lysejko et al. | |
| 6,628,631 B1 * | 9/2003 | Mazawa | H04W 36/02 455/442 |
| 7,215,991 B2 | 5/2007 | Besson et al. | |
| 7,386,032 B2 | 6/2008 | Fitton et al. | |
| (Continued) | | | |

FOREIGN PATENT DOCUMENTS

CA   2384877 A1   3/2001

OTHER PUBLICATIONS

International Search Report and Written Opinion in PCT/US2021/050174, mailed Jul. 17, 2023 (12 pages).

*Primary Examiner* — Young T. Tse
(74) *Attorney, Agent, or Firm* — Bookoff McAndrews, PLLC

(57) ABSTRACT

Systems, techniques, and devices are disclosed and may include a first sensor configured to generate a first data stream, a second sensor configured to generate a second data stream, and at least one processor and at least one non-transitory computer readable medium storing data stream management instructions. When executed by the at least one processor, the instructions causes the at least processor to receive the first data stream and the second data stream, spread the first data stream using a first code to generate a first coded data stream, spread the second data stream using a second code to generate a second coded data stream, combine the first coded data stream and the second coded data stream to generate a combined data stream, modulate the combined data stream to generate a modulated data stream, and transmit the modulated data stream via a single channel.

20 Claims, 12 Drawing Sheets

(56) References Cited

U.S. PATENT DOCUMENTS

| | | |
|---|---|---|
| 7,681,214 B2 | 3/2010 | Yousef et al. |
| 9,270,919 B2 | 2/2016 | Amling et al. |
| 2007/0291634 A1 | 12/2007 | Kwon et al. |
| 2014/0257111 A1 | 9/2014 | Yamashita et al. |
| 2018/0343596 A1* | 11/2018 | Soro ...................... A61B 5/024 |
| 2021/0320907 A1 | 10/2021 | Kirkpatrick |

* cited by examiner

SINGLE STREAM PROTOCOL FOR MULTIPLE SENSOR MEDICAL SYSTEM

CROSS-REFERENCE TO RELATED APPLICATIONS

This application is a continuation of U.S. application Ser. No. 17/474,225, filed on Sep. 14, 2021, which claims the benefit of priority from U.S. Provisional Application No. 63/079,069, filed on Sep. 16, 2020, which are incorporated by reference herein in their entireties.

TECHNICAL FIELD

Various aspects of the disclosure relate generally to image processing systems, devices, and related methods. Examples of the disclosure relate to systems, devices, and related methods that use multiple sensors, among other aspects.

BACKGROUND

Technological developments have given users of medical systems, devices, and methods, the ability to conduct increasingly complex procedures on subjects. One challenge in the field of minimally invasive surgeries is associated with using multiple data streams (e.g., multiple cameras, sensors, etc.), instead of a single data stream, to perform a single procedure. Transmission of multiple data streams can significantly increase the costs associated with a procedure and the related equipment as the transmission of multiple data streams is more resource intensive when compared to a single data stream. The additional resources can increase cost and implementation errors.

SUMMARY

Aspects of the disclosure relate to, among other things, systems, devices, and methods for efficient management of multiple real time data streams. Each of the aspects disclosed herein may include one or more of the features described in connection with any of the other disclosed aspects.

According to an example, a medical system may include a first sensor configured to generate a first data stream, a second sensor configured to generate a second data stream, and at least one processor and at least one non-transitory computer readable medium storing data stream management instructions that. When executed by the at least processor, the instructions causes the at least one processor to receive the first data stream and the second data stream, spread the first data stream using a first code to generate a first coded data stream, spread the second data stream using a second code to generate a second coded data stream, combine the first coded data stream and the second coded data stream to generate a combined data stream, modulate the combined data stream to generate a modulated data stream and transmit the modulated data stream via a single channel.

The data stream management instructions, when executed by the at least one processor, causes the at least one processor to receive the modulated data stream, de-modulate the modulated data stream to extract the combined data stream, apply the first code to extract the first data stream from the combined data stream, and apply the second code to extract the second data stream from the combined data stream.

The data stream management instructions, when executed by the at least one processor, causes the at least one processor to receive a first upstream data and a second upstream data, spread the first upstream data using a first upstream code to generate a first coded upstream data, spread the second upstream data using a second upstream code to generate a second coded upstream data, combine the first coded upstream data and the second coded upstream data to generate a combined upstream data, modulate the combined upstream data to generate a modulated upstream data, and transmit the modulated upstream data. The data stream management instructions may cause the at least one processor to apply a carrier-sense multiple access with collision avoidance (CSMA/CA) protocol to determine that a transmission channel is idle.

The stream management instructions stored in the at least one non-transitory computer readable medium may cause the at least one processor to receive a modulated upstream data, de-modulate the modulated upstream data to extract a combined upstream data, apply a first upstream code to extract a first upstream data from the combined upstream data, apply a second upstream code to extract a second upstream data from the combined upstream data, provide the first upstream data to the first sensor and the second upstream data to the second sensor.

The first upstream code may be the same as the first code. At least one of the first code and the second code may an orthogonal code. Spreading the first data stream includes performing an exclusive or (XOring) operation on the first code with the first data stream. The first code may be a pseudo-random binary code. The first data stream and the second data stream may be spread at a higher bit rate than the first data stream and the second data stream, respectively. The first code may be k bits wide and wherein the combined data stream includes less than or equal to k data streams. At least one of the first sensing device and the second sensing device may be located at a distal end of a shaft of the medical device, and the shaft may be configured for insertion into a body lumen. The modulated data stream may be transmitted using a single channel which may be a copper channel, a fiber channel, or air. The combined data streams may be modulated using a Quadrature Amplitude Modulation (QAM) modulator.

According to an example, a device may include a processor and a non-transitory computer readable medium storing data stream management instructions that, when executed by the processor, causes the processor to receive a modulated data stream from a modulator, de-modulate the modulated data stream to extract a combined data stream, the combined data stream comprising a first data stream spread using a first code and a second data stream spread using a second code, apply the first code to extract the first data stream from the combined data stream, wherein the first data stream is generated by a first sensor, and apply the second code to extract the second data stream from the combined data stream, wherein the first data stream is generated by a first sensor.

The data stream management instructions stored in the non-transitory computer readable medium may cause the processor to receive a first upstream data and a second upstream data, spread the first upstream data using a first upstream code to generate a first coded upstream data, spread the second upstream data using a second upstream code to generate a second coded upstream data, combine the first coded upstream data and the second coded upstream data to generate a combined upstream data, apply a carrier-sense multiple access with collision avoidance (CSMA/CA) protocol to determine that a transmission channel is idle, modulate the combined upstream data to generate a modulated upstream data, and transmit the modulated upstream data at a first time. The modulated data stream may be received via a single channel.

The data stream management instructions stored in the at least one non-transitory computer readable medium may cause the at least one processor to receive the modulated data stream at a first time, transmit the modulated upstream data at a second time after the first time, based on an indication from the CSMA/CA protocol, and receive a second modulated data stream at a third time after the second time.

According to an example, a method may include inserting a first sensor and a second sensor into a patient's body, generating a first data stream from the first sensor and a second data stream from the second sensor, spreading the first data stream using a first code to generate a first coded data stream, spreading the second data stream using a second code to generate a second coded data stream, combining the first coded data stream and the second coded data stream to generate a combined data stream, modulating the combined data stream to generate a modulated data stream, and transmitting the modulated data stream via a single channel.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Figure 1:
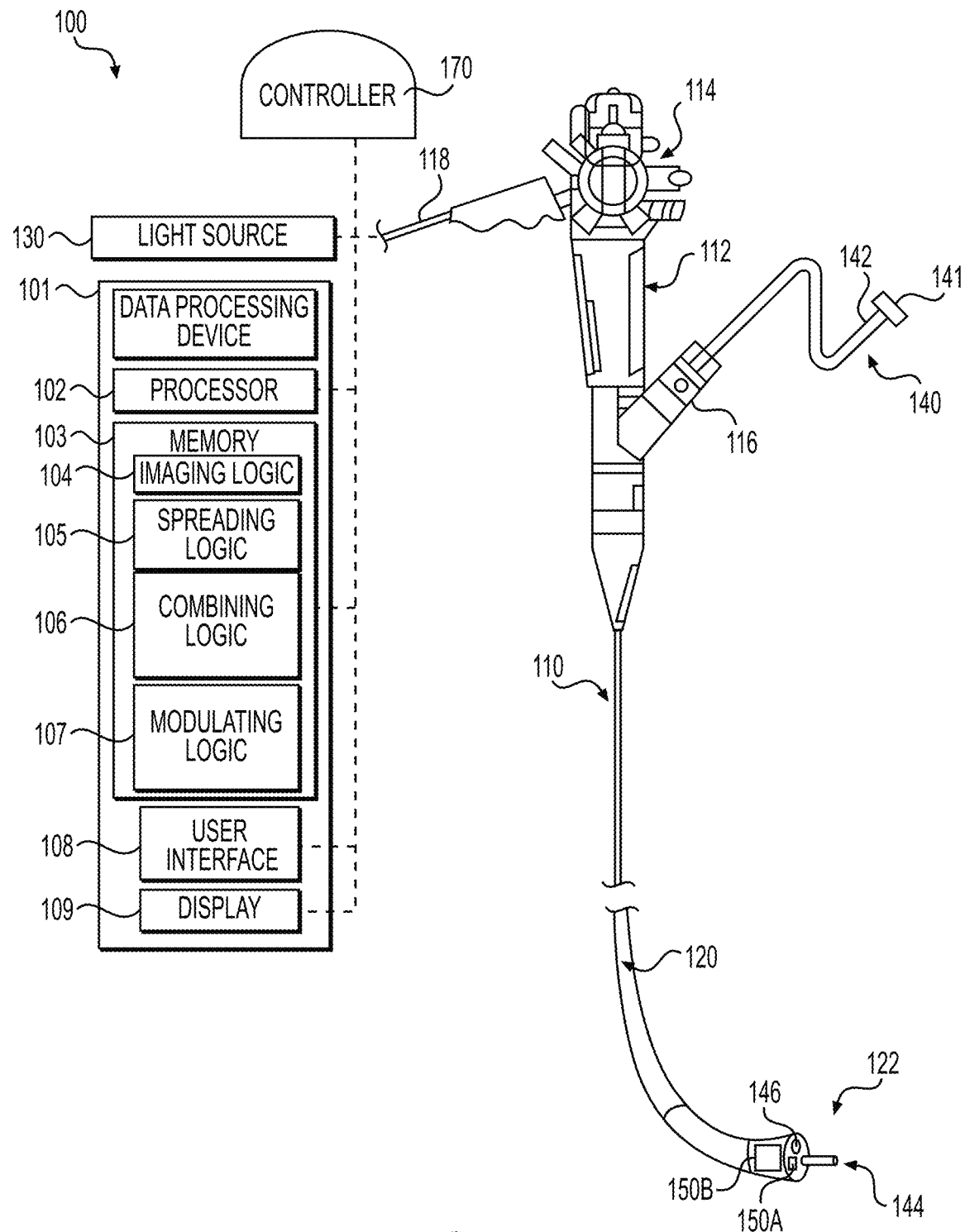
FIG. 1 is a schematic view of an exemplary medical system, according to aspects of this disclosure.

Examples of the disclosure include systems, devices, and methods for efficient management of multiple data streams such that they can be transmitted using a single connection. The multiple data streams may be provided via a wired or wireless connection and may be provided in real time with minimum lag and latency. Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the subject. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may be used to code and combine multiple data streams such that they can be modulated for transmission via a single channel. In some embodiments, a medical device may include multiple sensing devices to capture the multiple respective data streams for transmission to a controller for use during or in association with a medical procedure. Processors and non-transitory computer readable mediums for memory may be used to store and implement the disclosed subject matter. In embodiments, memory may include programmable instructions in accordance with a data streaming logic.

Examples of subject matter disclosed herein are directed to intra body procedures such as any procedure conducted using an invasive device such as a scope, endoscope, duodenoscope, gastroscope, colonoscope, ureteroscope, bronchoscope, catheter, probe, or the like, or a combination thereof. The procedure may include the use of multiple sensing devices (e.g., imaging components, sensing components, etc.) during the procedure. For example, an endoscope may include a distal tip that has a front facing imager and a side facing imager. Accordingly, a corresponding endoscopy may be conducted using both the front facing imager and the side facing imager. Each sensing device of the multiple sensing devices may generate a corresponding data stream. Each data stream may be individually provided to a receiving component (e.g., a controller). However, providing multiple data streams via multiple connections may result in use of additional resources (e.g., multiple contacts to transmit the location from a signal generating component such as a handle to a controller, multiple wires or connections, as well as additional components to facilitate the transmission and/or receipt of the multiple signals).

According to implementations of the disclosed subject matter, the efficient management of multiple data streams may use a single stream protocol (SSP). The SSP may be implemented to allow multiple data streams (e.g., from multiple sensing devices on a scope or other device(s)) to be combined and modulated such that a single data stream is generated and transmitted. The single data stream may be provided to a receiving component (e.g., a controller) via a single connection.

The implementations disclosed herein provide numerous technical benefits including use of optimized bandwidth (e.g., by using the spread spectrum via orthogonal codes, as disclosed herein), signal integrity (e.g., by using the modulation techniques disclosed herein), data stream efficiency (e.g., via a single wireless or wired point to point contact), and reduction in resources. Additionally, generating a single modulated data stream based on two or more data streams (e.g., two image streams) enables efficient wireless transmission of the single modulated data stream which can then be demodulated and split to receive the original two or more data streams. By transmitting the single modulated data stream, any differences in lag or latency between the two or more data streams, that would be present if using conventional techniques of transmitting each of the two or more data streams, are mitigated or eliminated.

FIG. 1 shows a schematic depiction of a medical system 100 in accordance with an example of this disclosure. The medical system 100 may include one or more light sources 130, a data processing device 101, a medical instrument 110, a medical device 140, and a controller 170. The data processing device 101 may be communicatively coupled to the medical instrument 110 by, for example, a wired connection, a wireless connection, and the like. In examples, the data processing device 101 is a computer system incorporating a plurality of hardware components that allow the data processing device 101 to receive data (e.g., image sensor data), process information (e.g., wavelength data), and/or generate a processed image for outputting to a user of the medical system 100. Illustrative hardware components of the data processing device 101 may include at least one processor 102, at least one memory 103, at least one user interface 108, and at least one display 109.

Although a single data processing device 101 is shown, it will be understood that medical system 100 may include multiple data processing devices and one or more physical locations. For example, the handle 112 of the medical instrument 110 of the medical system 100 may include a data processing device 101. Additionally, the controller 170 of the medical system 100 may also include a data processing device 101. As an example, the handle 112 may receive multiple data streams via sensors 150A and 150B (e.g., as also shown in different configurations in FIGS. 2A-2C) and a data processing device 101 of the handle 112 may spread, combine, and/or modulate the multiple data streams. According to implementations, one or more sensors (e.g., sensors 150A and 150B) may be disposed at different locations on the medical instrument 110 such as at different locations on the medical instrument 110, shaft 120, tip 122, etc. A modulated data stream may be transmitted to the controller 170 (e.g., via a wireless or wired transmission) where a data processing device 101 of the controller 170 may demodulate and split the modulated data stream such that the multiple data stream generated by the sensors 150A and 150B can be utilized via the controller 170 (e.g., may be provided to a health care professional as two separate sensed data streams).

The processor 102 of the data processing device 101 may include any computing device capable of executing machine-readable instructions, which may be stored on a non-transitory computer-readable medium, such as, for example, the memory 103 of the data processing device 101. By way of example, the processor 102 may include a controller, an integrated circuit, a microchip, a computer, and/or any other computer processing unit operable to perform calculations and logic operations required to execute a program. As described in greater detail herein, the processor 102 is configured to perform one or more operations in accordance with the instructions stored on the memory 103, such as, for example, an imaging logic 104, a spreading logic 105, a combining logic 106, a modulating logic 107, and the like. It will be understood that some or all of the components shown associated with the data processing device 101 may be implemented as hardware, firmware, and/or software.

The memory 103 of the data processing device 101 may include a non-transitory computer readable medium that stores machine-readable instructions thereon, such as, for example, the imaging logic 104, the spreading logic 105, the combining logic 106, the modulating logic 107, or the like.

Figure 2A:
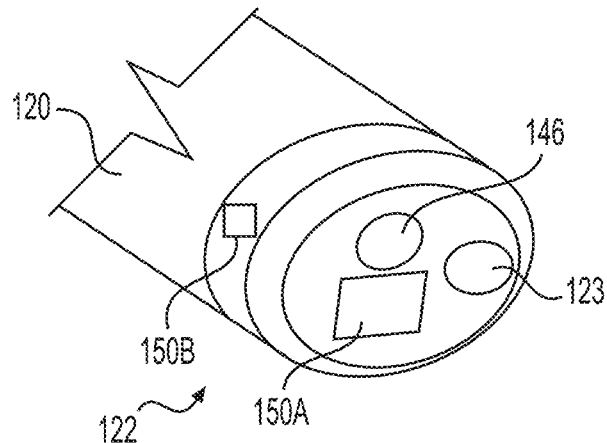
FIG. 2A is a partial perspective view of a medical device of the medical system of FIG. 1 including multiple sensors, according to aspects of this disclosure.
Figure 2B:
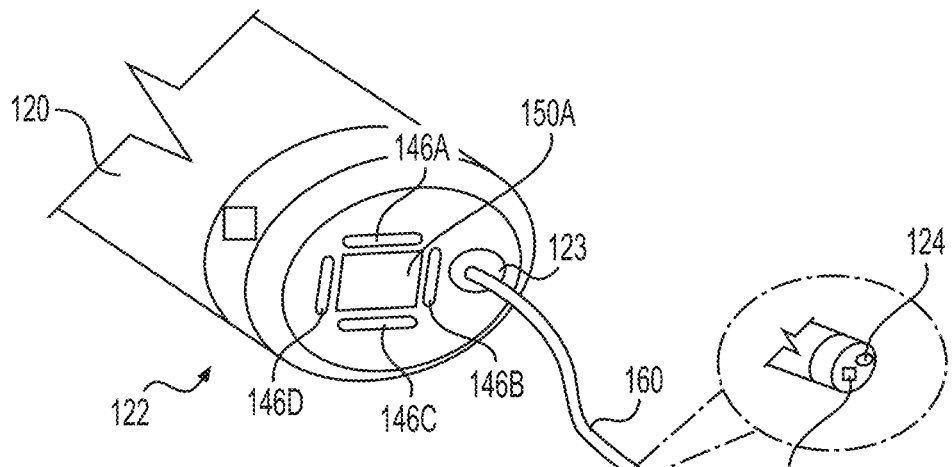
FIG. 2B is a partial perspective view of another medical device of the medical system of FIG. 1 including multiple sensors, according to aspects of this disclosure.
Figure 2C:
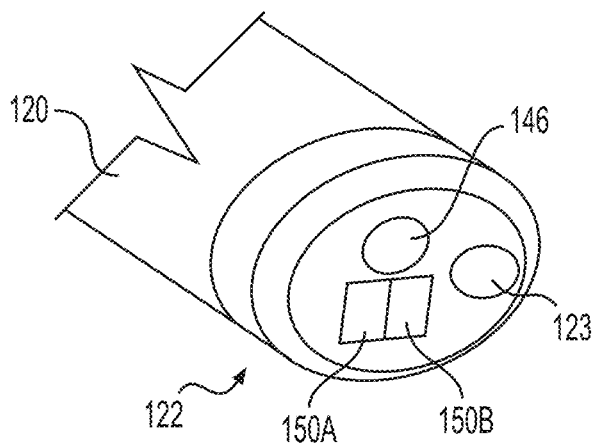
FIG. 2C is a partial perspective view of another medical device of the medical system of FIG. 1 including multiple sensors, according to aspects of this disclosure.

The imaging logic 104 may include executable instructions that allow the medical system 100 to capture raw digital images by activating one or more components of the medical instrument 110, such as, for example, one or more sensors 150A and/or 150B as shown in FIGS. 2A-2C.

The spreading logic 105 may include executable instructions that allow the medical system 100 to process data streams by spreading the data streams using a spreading sequence. Although spreading sequences such as orthogonal codes are generally disclosed herein, it will be understood that the orthogonal codes may refer to any applicable spreading sequences for spreading data streams (e.g., pseudo-random number (PN) binary codes, pseudo-random noise codes, etc.). The orthogonal codes may be k bits wide, and the number of data streams (e.g., sensed data streams, upstream data, etc.) may equal k, according to an implementation. A combined data stream, as further disclosed herein, may be generated from the up to k different data streams. For example, up to k different sensors may each generate a data stream, and the different data streams may be spread using respective orthogonal codes, each having k bits, such that each of the spread data streams can be combined into one combined data stream.

The spreading logic 105 may further include executable instructions that allow the medical system 100 to split demodulated data streams such that demodulated data streams are split using the same respective orthogonal codes to extract the original data streams.

The combining logic 106 may include executable instructions that allow the medical system 100 to combine coded data streams to generate a combined coded data stream. The combining logic 106 may enable combining multiple data streams from multiple different sources. As further discussed herein, the combining logic 106 may, for example, combine coded data streams (e.g., coded using the spreading logic 105, including the orthogonal codes) that are generated by different sensors (e.g., sensors 150A and 150B).

The modulating logic 107 may include executable instructions that allow the medical system 100 to vary one or more properties of a periodic waveform, called the carrier signal, with a modulating signal such as the coded data streams. The modulating logic 107 may use a modulator, as further disclosed herein. The modulating logic 107 may enable the data processing device 101 to convey multiple data streams by changing (modulating) the amplitudes of two data streams (e.g., by using a quadrature amplitude modulation (QAM) (e.g., QAM-64, QAM-128, etc.), an amplitude-shift keying (ASK) digital modulation scheme, an amplitude modulation (AM) analog modulation scheme, and/or the like). Multiple data streams of the same frequency may be out of phase with each other by, for example, 90°, a condition known as orthogonality or quadrature. A transmitted signal may be generated by modulating the multiple data streams together.

The modulating logic 107 may further include executable instructions that allow the medical system 100 to demodulate modulated data streams such that the modulated data streams are coherently separated (i.e., demodulated) due to, for example, their orthogonality property.

In some embodiments, the imaging logic 104, the spreading logic 105, the combining logic 106, and/or the modulating logic 107 may include executable instructions that allow the medical system 100 to execute management of multiple data streams automatically without requiring user input. For example, one or more components of the medical system 100 may determine that multiple data streams are available (e.g., via two or more sensing devices becoming activated) and, based on the detection, may automatically initiate management of the multiple data streams, as disclosed herein. In other embodiments, the data processing device 101 may be configured to receive user inputs to initiate the management of the multiple data streams, such as, for example, from a user interface 108 of the data processing device 101 (e.g., a user activating multiple sensing devices via the user interface 108). It should be appreciated that, in some embodiments, the user interface 108 may be a device integral with the data processing device 101, and in other embodiments, the user interface 108 may be a remote device in communication (e.g., wireless, wired, etc.) with the data processing device 101.

Various programming algorithms and/or data that support an operation of the medical system 100 may reside in whole or in part in the memory 103. The memory 103 may include any type of computer readable medium suitable for storing data and algorithms, such as, for example, random access memory (RAM), read only memory (ROM), a flash memory, a hard drive, and/or any device capable of storing machine-readable instructions. The memory 103 may include one or more data sets, including, but not limited to, image data from one or more components of the medical system 100 (e.g., the medical instrument 110, the medical device 140, etc.).

The medical instrument 110 may be configured to facilitate positioning one or more components of the medical system 100 relative to a subject (e.g., a patient), such as, for example, the medical device 140. In embodiments, the medical instrument 110 may be any type of endoscope, duodenoscope, gastroscope, colonoscope, ureteroscope, bronchoscope, catheter, or other delivery system, and may include a handle 112, an actuation mechanism 114, at least one port 116, and a shaft 120. An umbilicus 118 of the medical instrument 110 may have one or more lumens (not shown) that communicate with one or more lumens of one or more other components of the medical system 100. For example, umbilicus 118 my electrically connect 101, data processing device 101, light sources 130, and/or controller 170 to other components of medical instrument 110, including sensors 150A and 150B. The handle 112 further includes the at least one port 116 that opens into the one or more lumens of the handle 112. As described in further detail herein, the at least one port 116 is sized and shaped to receive one or more instruments therethrough, such as, for example, the medical device 140 of the medical system 100. Additionally, FIG. 2B shows an instrument 160 extend through an opening 123 of the shaft 120. The instrument 160 may be provided via the at least one port 116 and a corresponding lumen of the handle 112.

The shaft 120 of the medical instrument 110 may include a tube that is sufficiently flexible such that the shaft 120 is configured to selectively bend, rotate, and/or twist when being inserted into and/or through a subject's tortuous anatomy to a target treatment site. The shaft 120 may have one or more lumens (not shown) extending therethrough that include, for example, a working lumen for receiving instruments (e.g., the medical device 140). In other examples, the shaft 120 may include additional lumens such as a control wire lumen for receiving one or more control wires for actuating one or more distal parts/tools (e.g., an articulation joint, an elevator, etc.), a fluid lumen for delivering a fluid, an illumination lumen for receiving at least a portion of an illumination assembly (not shown), and/or an imaging lumen for receiving at least a portion of an imaging assembly (not shown).

The medical instrument 110 may further include a tip 122 at a distal end of the shaft 120. In some embodiments, the tip 122 may be attached to the distal end of the shaft 120, while in other embodiments the tip 122 may be integral with the shaft 120. For example, the tip 122 may include a cap configured to receive the distal end of the shaft 120 therein. The tip 122 may include one or more openings that are in communication with the one or more lumens of the shaft 120. For example, the tip 122 may include a working opening 123 through which the medical device 140 may exit from a working lumen of the shaft 120. It should be appreciated that other one or more openings at the tip 122 of the shaft 120 are not shown. The actuation mechanism 114 of the medical instrument 110 is positioned on the handle 112 and may include one or more knobs, buttons, levers, switches, and/or other suitable actuators. The actuation mechanism 114 is configured to control at least a deflection of the shaft 120 (e.g., through actuation of a control wire).

The medical device 140 of the medical system 100 may include a catheter having a longitudinal body 142 between a proximal end 141 of the medical device 140 and a distal end 144 of the medical device 140. The longitudinal body 142 of the medical device 140 may be flexible such that the medical device 140 is configured to bend, rotate, and/or twist when being inserted into a working lumen of the medical instrument 110. The medical device 140 may include a handle at the proximal end 141 of the longitudinal body 142 that may be configured to move, rotate, and/or bend the longitudinal body 142. Further, the handle at the proximal end 141 of the medical device 140 may define one or more ports (not shown) sized to receive one or more tools through the longitudinal body 142 of the medical device 140.

The medical instrument 110 may be configured to receive the medical device 140 via the at least one port 116, through the shaft 120 via a working lumen, and to the working opening 123 at the tip 122. In this instance, the medical device 140 may extend distally out of the working opening 123 and into a surrounding environment of the tip 122, such as, for example, at a target treatment site of a subject as described in further detail below. The distal end 144 of the medical device 140 may extend distally from the tip 122 in response to a translation of the longitudinal body 142 through the working lumen of the shaft 120. The medical device 140 may include one or more end effectors (not shown) at the distal end 144 of the longitudinal body 142, for performing one or more operations at a target treatment site.

The medical instrument 110 may be further configured to receive the one or more light sources 130 through the shaft 120 via at least one of the lumens of the medical instrument 110 for connection to an optical fiber 146. In the example, the one or more light sources 130 are shown as a separate component from the data processing device 101 such that the light sources 130 are coupled to the medical instrument 110 separately from the data processing device 101 (e.g., via a cable). It should be appreciated that, in other embodiments, the one or more light sources 130 may be included on the data processing device 101 such that the light sources 130 may be communicatively coupled to the medical instrument 110 with the data processing device 101.

Referring now to FIGS. 2A-2C, the tip 122 of the medical instrument 110 is depicted in accordance with one or more examples of this disclosure. Referring initially to FIG. 2A, in one embodiment, the tip 122 of the medical instrument 110 may include an optical fiber 146 and sensors 150A and 150B at the tip 122. In this example, the optical fiber 146 may be coupled to the one or more light sources 130 of the medical system 100, such that each of the one or more light sources 130 may transmit light through the single, optical fiber 146. Although not shown, it should be appreciated that multiple light sources 130 may be coupled to the optical fiber 146 via a fiber splitter/combiner. Alternatively, one or more LEDs may be positioned at the tip 122, and coupled to light sources 130 via a wired or wireless connection. The optical fiber 146 of the medical instrument 110 may be configured and operable to deliver various amplitudes of light, from the one or more light sources 130, distally from the tip 122 of the shaft 120.

The sensors 150A and 150B of the medical instrument 110 may be communicatively coupled to the data processing device 101 of the medical system 100, such as, for example, via a wired connection, a wireless connection, and/or the like. The sensors 150A and/or 150B may be any applicable sensor such as an image or video sensor, an ultrasound sensor, a fluoroscopy sensor, an electromagnetic sensor, a direct imager, a pH sensor, a pressure sensor, a multiple degree of freedom sensor, lower resolution sensor data (e.g., electromagnetic navigation), or the like. Although the multiple sensors are generally shown herein as being a part of medical instrument 110, one or more sensors may be located external to the medical instrument 110 such in an overhead tube crane (OTC). Additionally, as shown in FIG. 2B, one or more sensors (e.g., sensor 150A) may be part of a mother instrument (e.g., shaft 120 of medical instrument 110) and one or more other sensors (e.g., sensor 150B) may be part of a daughter instrument (e.g., instrument 160).

As shown in FIG. 2A, the sensor 150A may be a forward facing sensor whereas the sensor 150B may be a peripheral sensor, or a side-facing sensor. Sensors 150A, 150B may be any combination of forward or side-facing sensors. The sensors 150A and/or 150B may be configured and operable to capture raw images (e.g., a digital images) or other sensed data of a surrounding environment of the tip 122 of the shaft 120. In some embodiments, the sensors 150A and/or 150B may include an image sensor, such as, for example, an RGB (i.e., red-green-blue) digital sensor, an RGB-Ir (i.e., red-green-blue-infrared) digital sensor, a monochrome sensor, and/or the like. The sensors 150A and/or 150B may include one or more components for filtering colors from white light, ultraviolet light, near-infrared light, and/or other wavelengths within or beyond a visible spectrum.

According to an implementation, as shown in FIG. 2B, the medical instrument 110 may include a multicolor LED assembly at the tip 122 of the shaft 120. In this instance, the multicolor LED assembly may include one or more light-emitting diodes (hereinafter LEDs) 146A, 146B, 146C, 146D disposed in an annular array about the image sensor 150. Each of the LEDs 146A, 146B, 146C, 146D may be configured and operable to transmit a different light wavelength and/or amplitude (e.g., color) relative to one another.

As also shown in FIG. 2B, a working opening 123 extending from a working lumen of the shaft 120 may be used to insert an instrument 160. The instrument 160 (a "daughter" instrument) may be any applicable instrument such as one or more of a scope, a biopsy instrument, an irrigation instrument, a filtration instrument, or the like. The instrument 160 may include a sensor 150B such that multiple data streams may be generated from the distal end of the shaft 120 via the sensor 150A and also from the distal end of the instrument 160 via the sensor 150B. The instrument 160 may be controlled via handle 112 or via an independent set of controls.

As shown in FIG. 2C, the medical instrument 110 may include a multi sensor assembly at the tip 122 of the shaft 120. In this instance, the multi sensor assembly may include a first sensor 150A and a second sensor 150B. The sensor 150A and the sensor 150B may be the same or different types of sensors and may capture different data streams.

According to an example implementation of the subject matter, a duodenoscope having a first image sensor may be inserted into a patient's body. The duodenoscope may have a distal end with a tip (e.g., tip 122 of FIG. 1) that includes the first image sensor. The first image senor may be configured to obtain an ongoing video stream from the distal end of the duodenoscope. Additionally, as shown in FIG. 2B, a daughter scope (e.g., instrument 160) may be directed through a lumen and corresponding opening (e.g., opening 123) of the distal end of the duodenoscope. The duodenoscope may reach a first depth within a patient's digestive channel but may be too large to extend further than the first depth. The daughter scope may be smaller and may extend to a second depth deeper than the first depth. The daughter scope may have a distal end including a second image sensor, and the second image sensor may be configured to obtain an ongoing video stream from the distal end of the daughter scope.

As discussed herein, the first image sensor and the second image sensor may each generate a data stream (i.e., a first data stream and a second data stream, respectively). Electronic components including at least one processor within the medical system 100 of FIG. 1 (e.g., located in the handle 112) may receive the first data stream and the second data stream. The first data stream and the second data stream may each be spread using respective first orthogonal codes and second orthogonal codes such that a first coded data stream and a second coded data stream are generated from the first data stream and the second data stream. As further discussed herein, the coded data streams may have a higher bit rate then then data steams they are based on.

The first coded data stream and the second coded data stream may be combined and modulated to generate a single modulated data stream. The single modulated data stream may represent both the first data stream and the second data stream in a spread (e.g., coded) and combined format. The single modulated data stream may be transmitted, wirelessly or via a wired connection, to a controller (e.g., controller 170 of FIG. 1). The single modulated data stream may be transmitted via a single transmission channel, reducing complexity, cost, and resources.

The controller 170 may receive the single modulated data stream via the single transmission channel and may demodulate the single modulated data stream. Once demodulated, the combined data stream may be extracted, and the first orthogonal code and the second orthogonal code may be applied to the combined data stream. Application of the first orthogonal code and the second orthogonal code to the combined data stream may produce the original first data stream generated by the first image sensor at the distal end of the duodenoscope and the original second data stream generated by the second image sensor at the distal end of the daughter scope, respectively. As also disclosed herein, dual channel communication may be generated at the controller 170, and may be combined, modulated, and transmitted to the medical device via the same transmission channel used to transmit the single modulated data stream from the medical device to the controller.

Figure 3A:
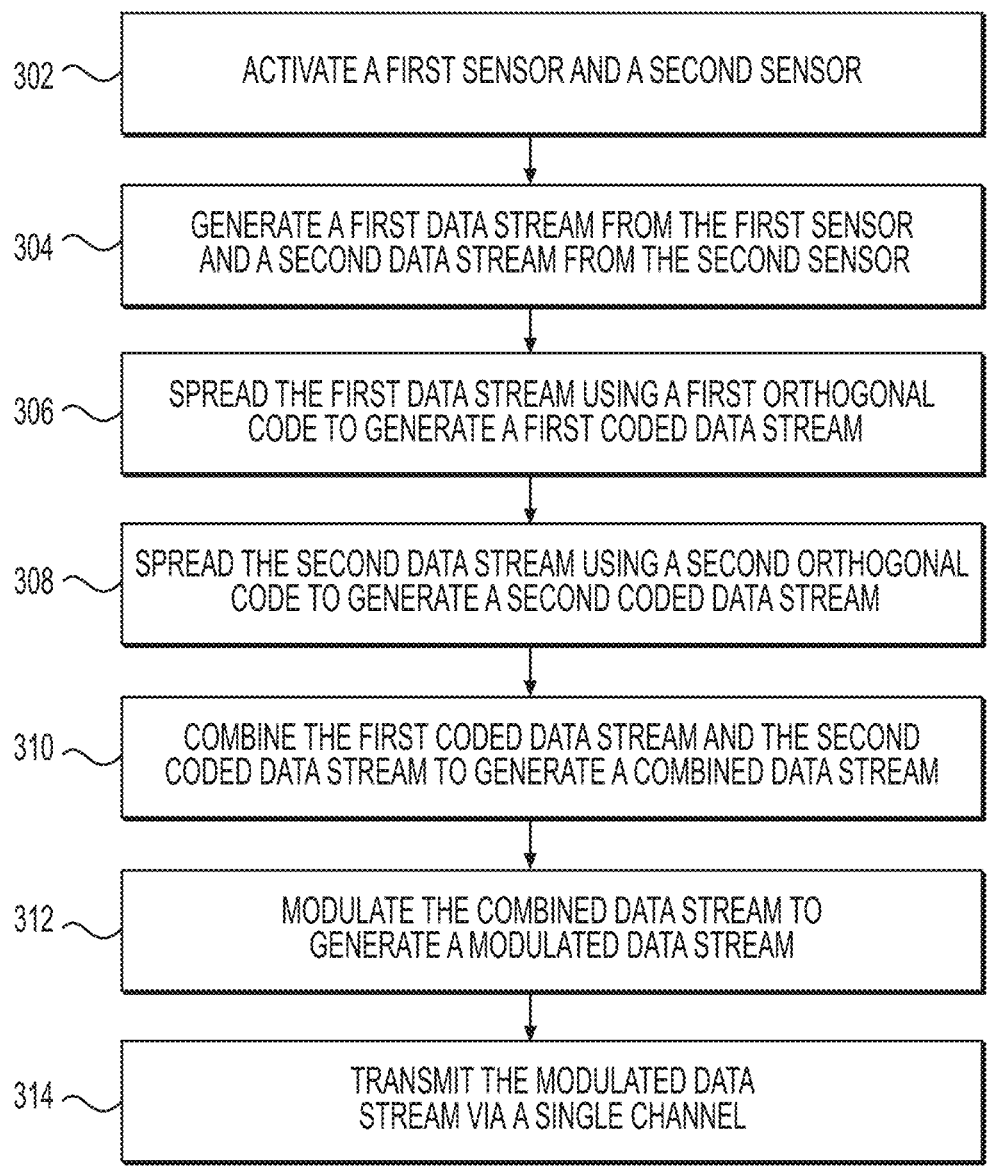
FIG. 3A is a flowchart for a single stream protocol transmission, according to aspects of this disclosure.

FIG. 3A shows a flowchart 300 for transmitting a modulated data stream via single channel, in accordance with a single stream protocol. At step 302, a first sensor (e.g., sensor 150A of FIGS. 1-2C) and a second sensor (e.g., senor 150B of FIGS. 1-2C) are activated. The first sensor 150A and the second sensor 150B may be activated by user input (e.g., user input provided via user interface 108) which may be provided, for example, prior to, during, or after a medical device (e.g., medical instrument 110) is inserted into a patient's body. Alternatively, the first sensor and the second sensor may be activated automatically upon a medical device (e.g., medical instrument 110) being powered or otherwise activated. Alternatively, the first sensor 150A and the second sensor 150B may activate automatically upon detecting that a medical device and/or the first sensor 150A or second sensor 150 is inserted into a patient's body (e.g., via one or more proximity sensors associated with the first and second sensor). It will be understood that although a first sensor 150A and second sensor 150B are generally described herein, additional sensors may be used and implemented in accordance with the disclosed subject matter such that the disclosed subject matter is not limited to two sensors in any way.

Figure 3B:
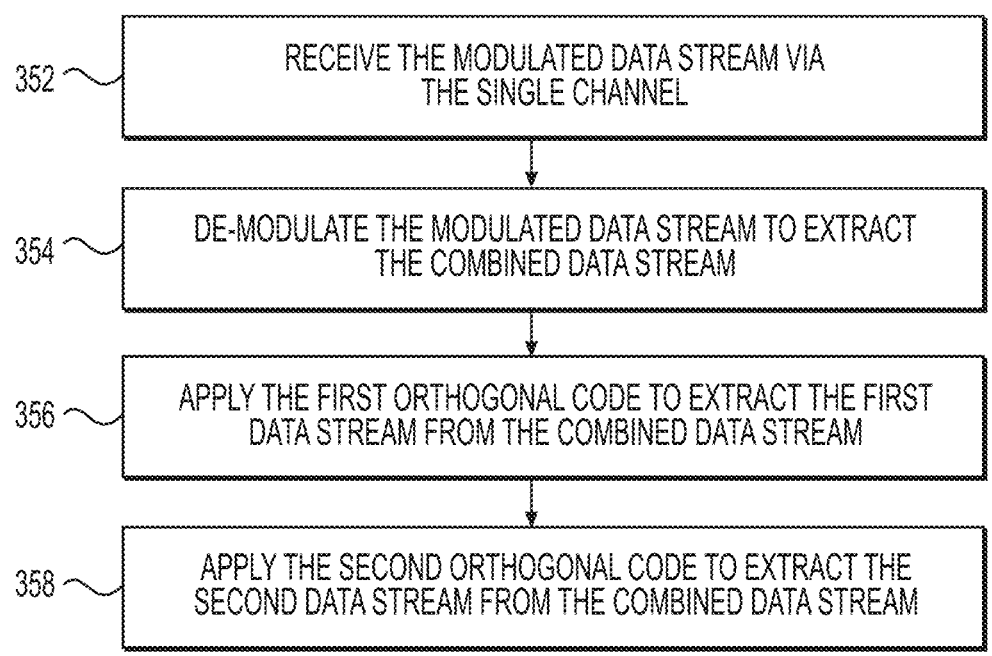
FIG. 3B is a flowchart for receiving the single stream protocol transmission of FIG. 3A, according to aspects of this disclosure.
Figure 4A:
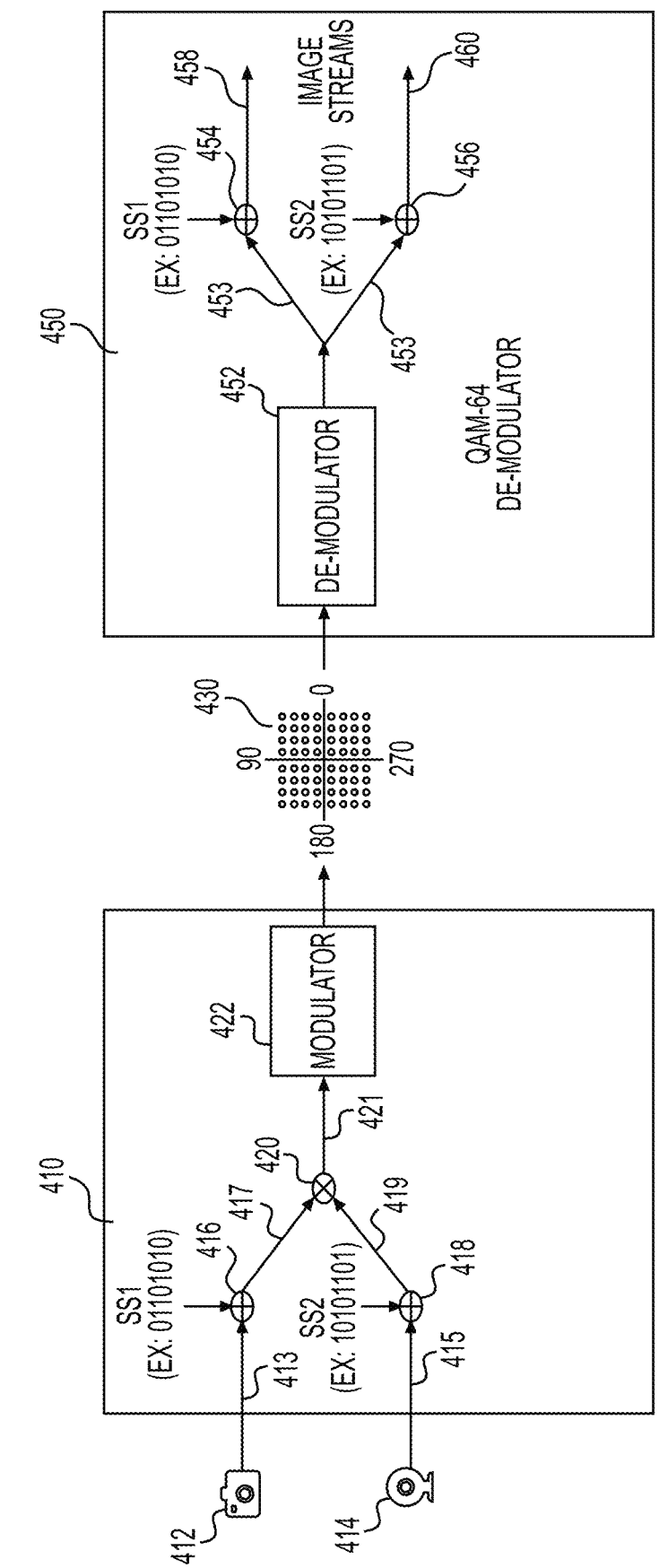
FIG. 4A is a diagram of a single stream protocol implemented in the medical system of FIG. 1, according to aspects of this disclosure.
Figure 4C:
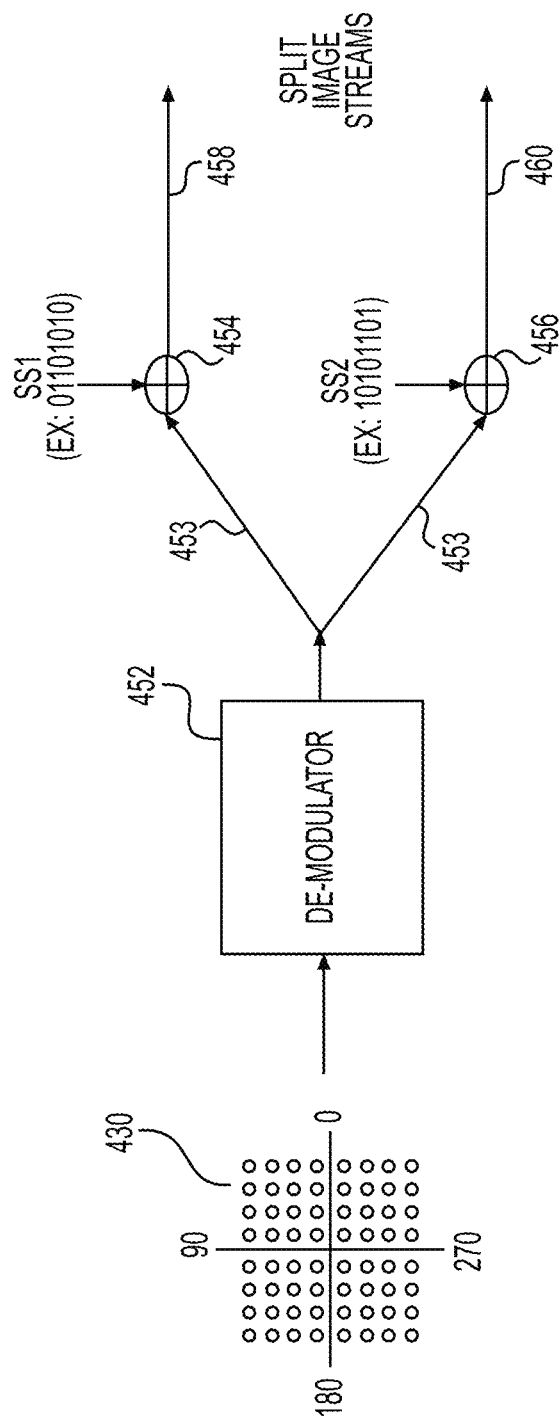
FIG. 4C is a diagram of another aspect of the single stream protocol of FIG. 4A, according to aspects of this disclosure.
Figure 4B:
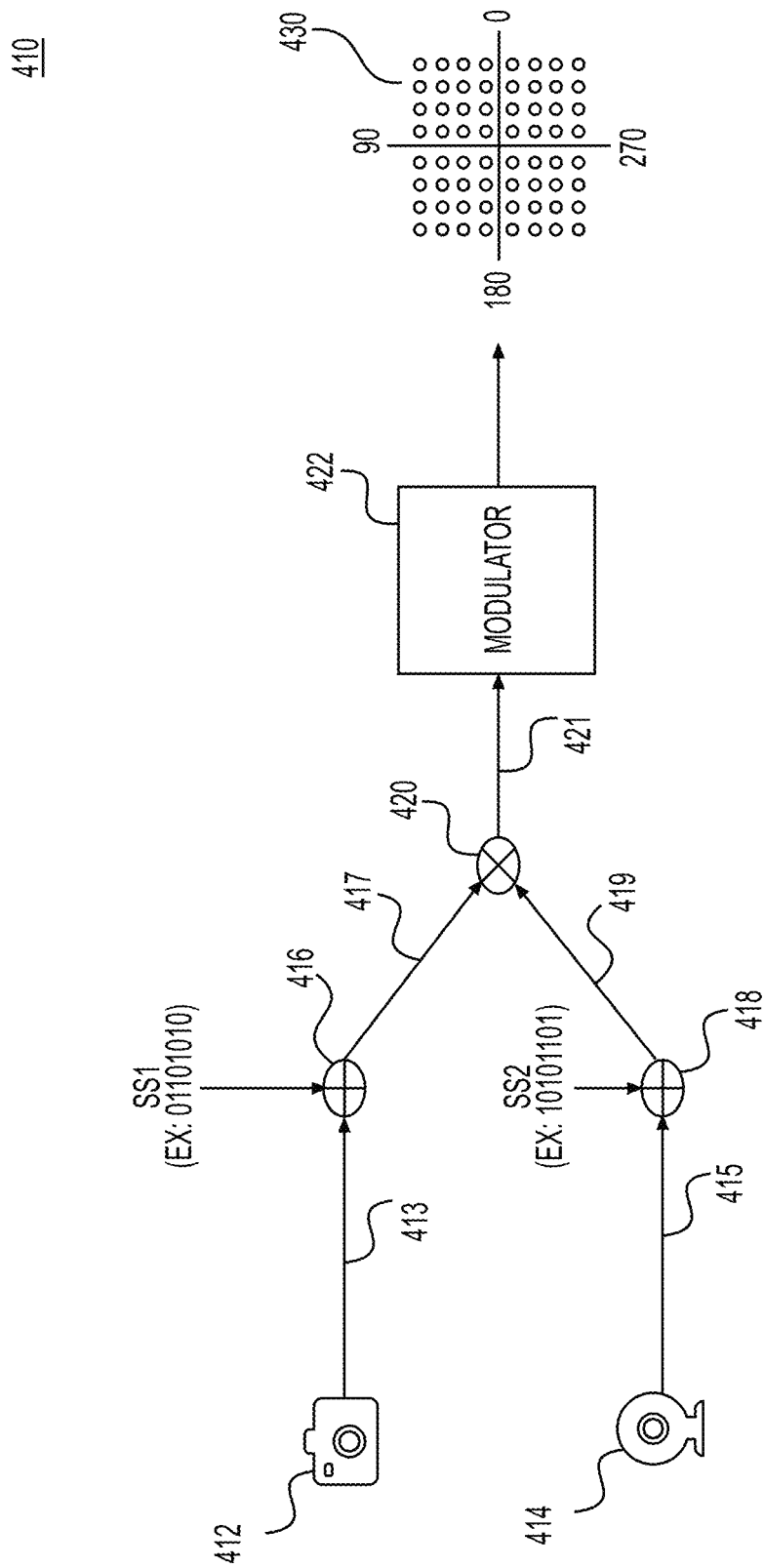
FIG. 4B is a diagram of an aspect of the single stream protocol of FIG. 4A, according to aspects of this disclosure.

FIGS. 4A-4C show diagrams for implementation of the single stream protocol of the flowchart 300 of FIG. 3A as well as the flowchart 350 of FIG. 3B, as further disclosed herein. The single stream protocol of FIGS. 3A-3B and FIGS. 4A-4C may be implemented using the medical system 100 of FIG. 1. FIG. 4A shows an overall single stream implementation 400 which includes the modulation implementation 410 for generating a single modulated data stream 430 and also includes the demodulation implementation 450 for generating the first data stream 458 and second data stream 460 from the single modulated data stream 430. For clarity, FIG. 4B shows the modulation implementation 410 for generating a single modulated data stream 430 of FIG. 4A and FIG. 4C shows the demodulation implementation 450 for generating the first data stream 458 and second data stream 460 from the single modulated data stream 430, of FIG. 4A. Accordingly, it will be understood that references made herein to either FIG. 4B or FIG. 4C also apply to FIG. 4A which shows the overall single stream implementation 400 that includes the modulation implementation 410 and the demodulation implementation 450.

FIG. 4B shows a first sensor 412 and a second sensor 414. As shown in FIGS. 2A-2C, the first sensor 412 and the second sensor 414 may be on the same surface, on adjacent surfaces, or on separate surfaces. For example, FIG. 2A shows sensor 150A, which may correspond to the first sensor 412, and sensor 150B, which may correspond to second sensor 414, on adjacent surfaces of a tip 122. As another example, FIG. 2B shows sensor 150A on a surface of the tip 122 and sensor 150B on a separate surface corresponding to a daughter device, instrument 160. As another example, FIG. 2C shows sensors 150A and 150B on the same surface of tip 122. It will also be understood that, according to an implementation, either the first sensor 412 and/or the second sensor 414 may be separate from a given medical device (e.g., medical instrument 110). For example, either the first sensor 412 and/or the second sensor 414 may be located external to the medical device that is inserted into the patient's body. As a specific example, either the first sensor 412 and/or the second sensor 414 may be a heartbeat sensor that senses the heartbeat of a patient via the surface of the patient's chest.

As stated, at step 302 of FIG. 3A, the first sensor 412 and the second sensor 414 may be activated. At step 304, the first sensor 412 may generate a first data stream 413 and the second sensor 414 may generate a second data stream 415. The first data stream 413 and the second data stream 415 may be different data streams each generated by the respective first sensor 412 and the second sensor 414. According to an implementation, when either the first sensor 412 or the second sensor 414 is not actively sensing, a null data stream may be generated by the respective sensor. The null data stream may trigger an indication of an error (e.g., a user may be provided an error alert indicating that the respective sensor is not actively sensing at a given time) or may simply be ignored as an expected result of a current aspect of a procedure.

The first data stream 413 and the second data stream 415 may be generated by the respective sensors 412 and 414 based on intermediate or continuous operation of the sensors 412 and 414 to capture sensed data that is used to generate the first data stream 413 and the second data stream 415. As an example, the first sensor 412 may be a video sensor that captures a constant video signal as the medical instrument 110 is inserted into a patient's body. Accordingly, the first data stream 413 may be a constant video stream captured via the video sensor.

In conventional systems, first and second data streams may be provided directly to a controller. However, such a conventional system requires multiple connections to transmit and receive the multiple data streams, thus increasing the number of resources required to receive the streams. Further, such a conventional system is susceptible to data breaches causing a lack of integrity since the data streams would directly be transferred from one component to another. Further still, implementing such a system wirelessly would require additional resources, each to wirelessly transmit a separate stream, and such transmissions would not be synchronized such that there may be different latency or lag between the multiple transmissions which may cause errors during a respective medical procedure.

At step 306 of FIG. 3A, the first data stream 413 may be spread (e.g., via application of the spreading logic 105 of FIG. 1) using a first orthogonal code. The spread operation may result in a first coded data stream 417. As shown in FIG. 4B, the first data stream 413 may be received at a first spreading component 416, and the first spreading component 416 may perform the spreading operation using the first orthogonal code. The first spreading component 416 may be based in hardware, software, or firmware and may be configured to continuously receive the first data stream 413 while the first sensor 412 is activated.

Similarly, at step 308 of FIG. 3A, the second data stream 415 may be spread (e.g., via application of the spreading logic 105 of FIG. 1) using a second orthogonal code. The spread operation may result in a second coded data stream 419. As shown in FIG. 4B, the second data stream 415 may be received at a second spreading component 418, and the second spreading component 418 may perform the spreading operation using the second orthogonal code. The second spreading component 418 may be based in hardware, software, or firmware and may be configured to continuously receive the second data stream 415 while the second sensor 414 is activated.

The first orthogonal code and the second orthogonal code each used to spread the first data stream 413 and the second data stream 415, respectively, may be sequences of binary digits (e.g., sequence 01101010 as the first orthogonal code and 10101101 as the second orthogonal code, as shown in FIG. 4B). The spreading operation at steps 306 and 308 of FIG. 3A may be implemented using a direct-sequence spread spectrum (DSSS) scheme and may multiply (XOR) the first data stream 413 and the second data stream 415 by the respective first orthogonal code and second orthogonal code.

The bit rate of the orthogonal codes may be higher than that of the respective data streams such that a higher bandwidth of data is represented by the resulting coded data streams. To clarify, the bit rate of the resulting first coded data stream 417 and the second coded data stream 419 may be the same as the higher bit rate first orthogonal code and the second orthogonal code, respectively, when compared to the first data stream 413 and the second data stream 415. The higher bit rate may increase the transmitted data rate of the modulated data stream 430, as further disclosed herein, and may therefore increase the required bandwidth for communication. Additionally, the redundancy and security of the transmission may also increase. For example, applying the first and second orthogonal codes to spread the first data stream 413 and the second data stream 415 may result in the first coded data stream 417 and the second coded data stream 419 that exhibit noise like signal properties. The noise like properties of the first coded data stream 417 and the second coded data stream 419 may mitigate the risk associated with transmitting the resulting modulated data stream, as further disclosed herein. For example, wireless transmission of the modulated data stream 430 based on the noise like first coded data stream 417 and the second coded data stream 419 may mitigate the risk of the modulated data stream 430 from being intercepted and/or decrypted by unauthorized entities.

The properties of the modulated data stream 430 may provide immunity from various types of noise and multipath distortion. Additionally, the use of non-public first orthogonal code and second orthogonal code provides an added layer of security as only an entity with the first orthogonal code and second orthogonal code can obtain the decoded data streams 458 and 460, as further disclosed herein. Additionally, using different orthogonal codes (e.g., the first orthogonal code, the second orthogonal code, etc.) provides a lack of correlation between the different signals such that a controller (e.g., controller 170) can extract any individual signal using that signal's corresponding orthogonal code, as further discussed in FIG. 4C. Because of the high degree of redundancy provided by the spreading at steps 304 and 306, the de-spreading operation discussed in FIG. 4C is implanted despite the interference of multiple signals in the same bandwidth.

Figure 5:
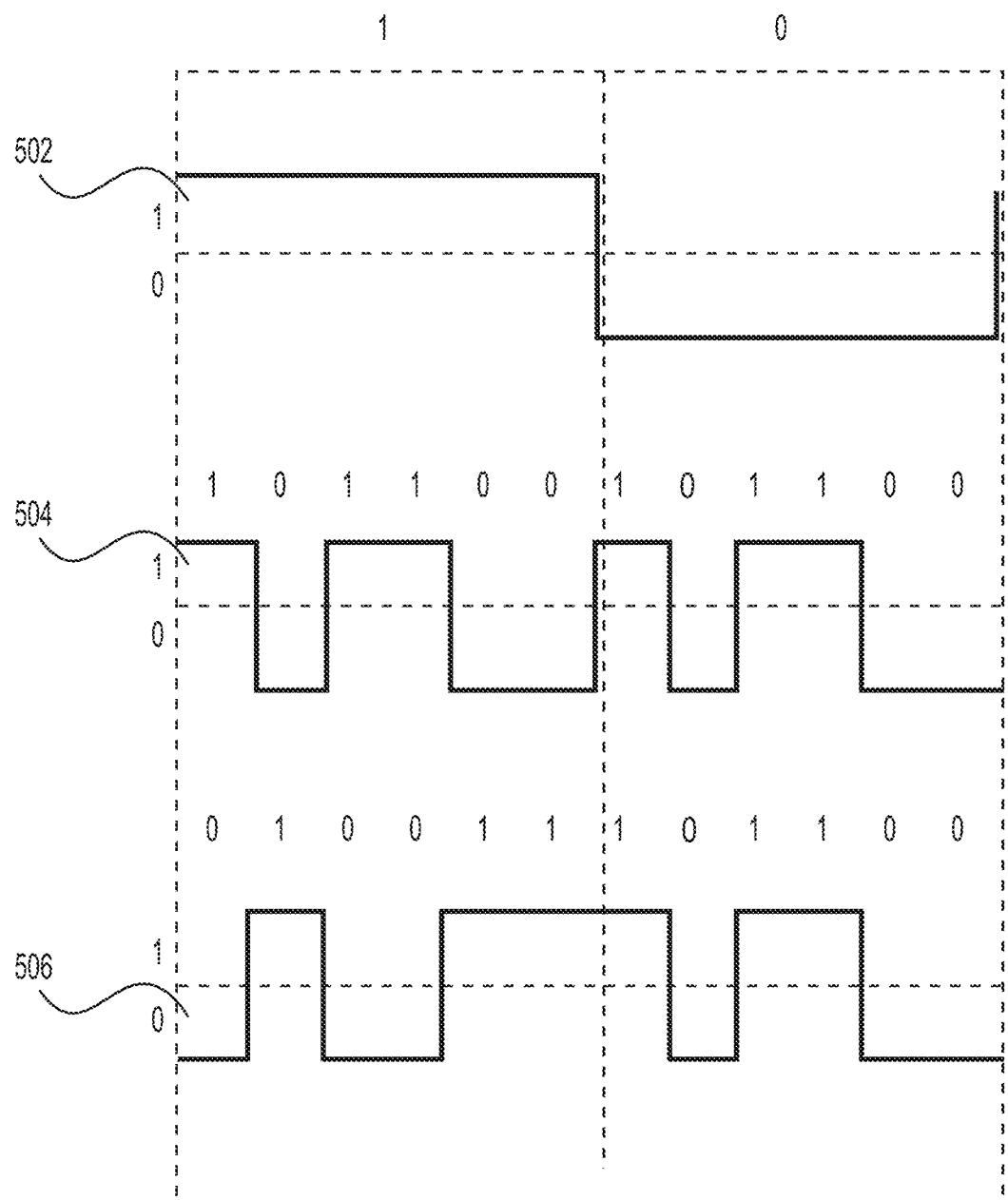
FIG. 5 is a diagram of an application of an orthogonal code to a data stream, according to aspects of this disclosure.

FIG. 5 shows an example diagram of an application (e.g., XOR multiplication) of an orthogonal code 504 to a data stream 502 to generate a coded data stream 506. As shown, the data stream 502 has a lower bit rate (e.g., two bits) represented by a 1 and a 0. The orthogonal code 504 has a higher bit rate (e.g., 6 bits for each bit of the data stream 502, for a total of 12 bits) than the data stream's lower bit rate. In this example, the orthogonal code 504 is 101100101100.

Upon X-ORing the data stream 502 with the orthogonal code 504, the resulting coded data stream is generated and has a sequence 010011101100. To clarify, by X-ORing the data stream 502 with the orthogonal code 504, the resulting coded data stream 506 produces a false value (e.g., 0) if the data stream 502 and the orthogonal code 504 have matching values. Similarly, the resulting coded data stream produces a truth value (e.g., 1) if the data stream 502 and the orthogonal code 502 have mismatched values.

At step 310 of FIG. 3A, the first coded data stream 417 and the second coded data stream 419 are combined into a combined data stream 421 using a combination component 420. The combination component 420 may be configured to constantly combine the first coded data stream 417 and the second coded data stream 419 as the respective coded data streams are being output by the first spreading component 416 and the second spreading component 418.

At step 312, the combined data stream 421 is provided to a modulator 422 that modulates the combined data stream 421 to generate the modulated data stream 430. The modulator 422 may be a QAM modulator (e.g., a QAM-16 modulator, a QAM-32 modulator, a QAM-64 modulator, a QAM-128 modulator, a QAM-256 modulator etc.), a frequency-shift keying (FSK) modulator, an orthogonal frequency-division multiplexing (OFDM) modulator, an application-specific integrated circuit (ASIC) modulator, etc.

The modulator 422 may be selected based on considering a balance between data throughput and signal to noise ratio required. As the order of the QAM signal is increased (e.g., a progressing from 16QAM to 128QAM), the data throughput achievable under ideal conditions also increases. However, a better signal to noise ratio is required to achieve optimal operation under the increased throughput. The modulator 422 of FIG. 4B may be a QAM-64 modulator, as indicated by the dot pattern for modulated data stream 430 shown in FIGS. 4A-4C. As the modulation order for the QAM filter increases, the distance between the points on the constellation decreases. Accordingly, small amounts of noise can cause greater errors in the modulated data stream 430. As the level of noise increases due to low signal strengths, the area covered by a point on the constellation also increases. However, if this area becomes larger than a threshold area, then the controller (e.g., controller 170) may be unable to determine on which position on the constellation the modulated data stream 430 was to be located, which may result in errors. Additionally, the higher the order of modulation for the QAM signal, the greater an amount of amplitude variation is present on the modulated data stream 430.

Continuing the example shown in FIG. 4A, a QAM-64 modulator may allow a single modulated data stream 430 to represent 6 bits of data by manipulating the amplitude and phase of the wave into one of sixty four different discrete states. Accordingly, the techniques provided herein for combining multiple data streams along with modulating using a modulator 422 (e.g., QAM-64 modulator) provides the bandwidth capacity that allows multiple data streams to be consolidated, enabling a single stream to be transmitted to a controller (e.g., controller 170 of FIG. 1) via a single channel.

At step 314 of FIG. 3A, the modulated data stream 430 is transmitted via a single channel. According to an implementation, the single channel may be a wireless channel such that the modulated data stream 430 is transmitted using a wired component or wireless component (e.g., a transmit antenna, a transceiver, etc.). Because the modulated data stream 430 is generated based on multiple data streams (e.g., the first data stream 413 and the second data stream 415), transmitting the multiple data streams at once via the modulated data stream 430 mitigates or eliminates uneven lag or latency between the data streams. To clarify, because the modulated data stream 430 is transmitted (e.g., via handle 112 and umbilicus 118) and received (e.g., via a controller 170 of FIG. 1) via a single wired or wireless transmission channel, the underlying multiple data streams (e.g., the first data stream 413 and the second data stream 415) are transmitted and received at the same time. As an example, if the first data stream 413 is a video from a forward facing imager and if the second data stream 415 is a video from a peripheral imager, then it is beneficial for the two streams to be coordinated as, otherwise, a healthcare professional performing or supporting the procedure may not be able to properly conduct the procedure if the two available visual cues via the two data streams are temporally misaligned. Additionally, by transmitting the modulated data stream 430 wirelessly via a single channel, there may be a significant reduction in resources and, thus, related costs and opportunities for component failure. For example, transmitting the modulated data stream 430 wirelessly may remove the need for physical connectors and corresponding cables which can be costly and error prone.

According to an implementation, the single channel may be a single wired connection that provides the modulated data stream 430 from the modulator 422 to a controller (e.g., controller 170 of FIG. 1) via an electrical connector. The wired connection via a single channel may provide a reduction in resources as a single connector is required to provide the modulated data stream 430 from the modulator 422 to a controller (i.e., instead of multiple connectors, one each for each corresponding data stream). The wired connection may be provided using copper wiring and/or connector, using a fiber connection, or any other applicable wired connection, including a wired connection using umbilicus 118.

The modulated data stream 430 may be provided to a controller or other applicable component that enables the multiple data streams 413 and 415 to be utilized. For example, the modulated data stream 430 may be provided to a controller that facilitates the visualization of the multiple data streams 413 and 415 via a display. It will be understood that the controller, as applied herein, may be an intermediate component in the application of the multiple data streams 413 and 415 or may be the final component that applies the multiple data streams 413 and 415. The controller 170 may include a data processing device 101 including a modulating logic 107, a combining logic 106, and a spreading logic 105.

As shown in flowchart 350 of FIG. 3B, at step 352, the modulated data stream 430 of FIG. 4B and FIG. 4C may be received (e.g., by controller 170) via a single channel, as discussed herein. As an example, the modulated data stream 430 may be received by a receiving antenna or transceiver located at the controller 170.

FIG. 4C shows the demodulation implementation 450 of FIG. 4A. The demodulation implementation 450 may be implemented at controller 170 or any other applicable capital equipment. As shown in FIG. 4C, the modulated data stream 430 may be received at a de-modulator 452 that may de-modulate the modulated data stream 430 to extract the combined data stream 453. The de-modulator 452 may be a QAM de-modulator (e.g., a QAM-16 de-modulator, a QAM-32 de-modulator, a QAM-64 de-modulator, a QAM-128 de-modulator, a QAM-256 de-modulator etc.), a FSK de-modulator, OFDM de-modulator, an ASIC de-modulator, etc. The de-modulator 452 may be selected based on the modulator 422 such that the demodulation conducted at step 354 of FIG. 3B corresponds to the modulation conducted at step 312 of FIG. 3A.

De-modulating the modulated data stream 430 may provide the combined data stream 453 that corresponds to the combined data stream 421 and that includes the multiple data streams 413 and 415. According to an implementation, the combined data stream 453 may be identical or approximately identical to the combined data stream 421. According to another implementation, the combined data stream 453 may be a derivation or augmented version of the combined data stream 421. The combined data stream 453 may be provided such that it enables the extraction of the data streams 458 and 460, as further disclosed herein.

At step 356, the first orthogonal code used at step 306 may be applied (e.g., XOR multiplication) to the combined data stream 453. The first orthogonal code may be applied by a first extraction component 454. According to an implementation, the first extraction component 454 may be the same as or similar to the first spreading component 416. In the example provided in FIGS. 4A-4C, the first orthogonal code 01101010 may be XORed with the combined data stream 453 to extract the first data stream 458. According to an implementation, the first data stream 458 may be identical or approximately identical to the first data stream 413. According to another implementation, the first data stream 458 may be a derivation or augmented version of the first data stream 413. The first data stream 458 may be extracted such that it serves the same practical function as if the first data stream 413 was received at the controller 170.

Similarly, at step 358, the second orthogonal code used at step 308 may be applied (e.g., XOR multiplication) to the combined data stream 453. The second orthogonal code may be applied by a second extraction component 456. According to an implementation, the second extraction component 456 may be the same as or similar to the second spreading component 418. Additionally, according to an implementation, the first extraction component 454 and the second extraction component 456 may be the same. In the example provided in FIGS. 4A-4C, the second orthogonal code 10101101 may be XORed with the combined data stream 453 to extract the second data stream 460. According to an implementation, the second data stream 460 may be identical or approximately identical to the second data stream 415. According to another implementation, the second data stream 460 may be a derivation or augmented version of the second data stream 415. The second data stream 460 may be extracted such that it serves the same practical function as if the second data stream 415 was received at the controller 170.

As discussed herein, FIG. 5 shows an example diagram 500 of an application (e.g., XOR multiplication) of an orthogonal code 504 to a data stream 502 to generate a coded data stream 506. FIG. 5 also shows the reverse operation such that if the coded data stream 506 corresponds to the demodulated data stream 453, then XORing the coded data stream 506 with the orthogonal code 504 results in the data stream 502. In this example, the orthogonal code 504 is 101100101100. Upon X-ORing the coded data stream 506 with the orthogonal code 504, the resulting coded data stream 502 is generated and has a sequence 111111000000 or, if simplified, is the same as the lower bit rate 10.

The controller 170 may apply the first data stream 458 and the second data stream 460 in any applicable manner to support a given medical procedure. As an example, the first data stream 458 may be a video signal. and the second data stream may be a temperature sensor. Accordingly, a visual representation of the first data stream 458 may be shown on a display screen along with a temperature reading taken at the tip (e.g., tip 122 of FIG. 1) of a medical device (e.g., medical device 110) via the second data stream. According to another implementation, the controller may further transmit the first data stream 458 and the second data stream 460 to another component. The further transmission may be via a cloud server and may be received at a remote location separate from the location of the medical system 100.

According to an implementation of the disclosed subject matter, control settings may require upstream communication (e.g., sideband communication) from a controller (e.g., controller 170) back to the multiple sensors (e.g., the first sensor 412 and the second sensor 414 of FIGS. 4A-4C). Such an upstream communication may be conducted via the single stream protocol disclosed herein such that communication is generated via multiple channels from a controller (e.g., capital), converted to a single modulated signal, and provided to the multiple sensors via a single channel.

Figure 6A:
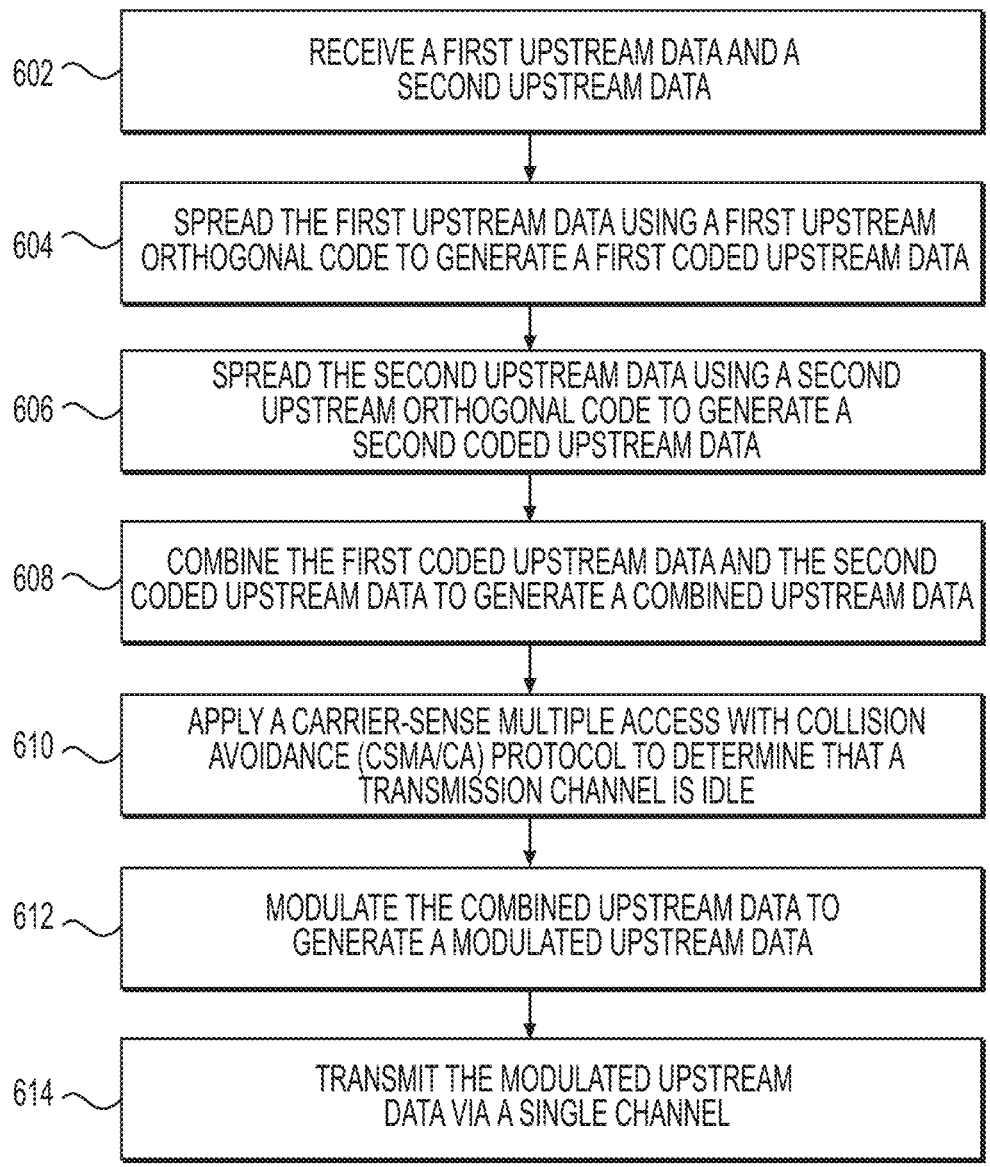
FIG. 6A is a flowchart for an upstream transmission via a single stream protocol, according to aspects of this disclosure.
Figure 6B:
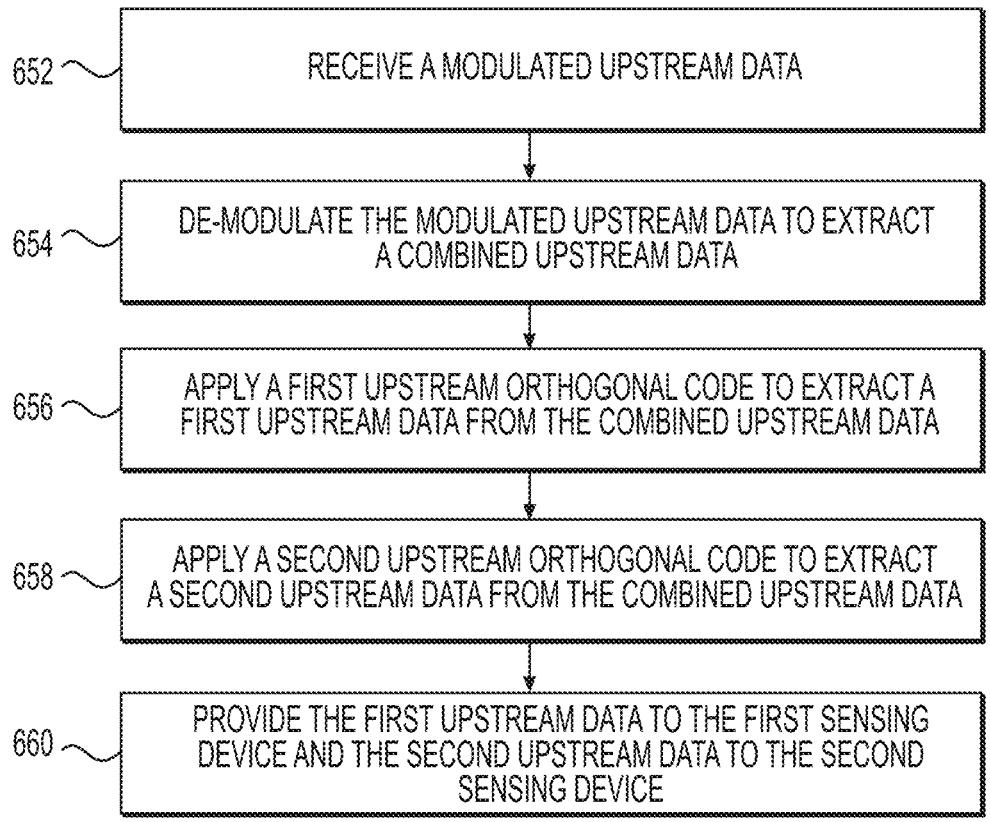
FIG. 6B is a flowchart for receiving the upstream transmission of FIG. 6A, via a single stream protocol, according to aspects of this disclosure.
Figure 7A:
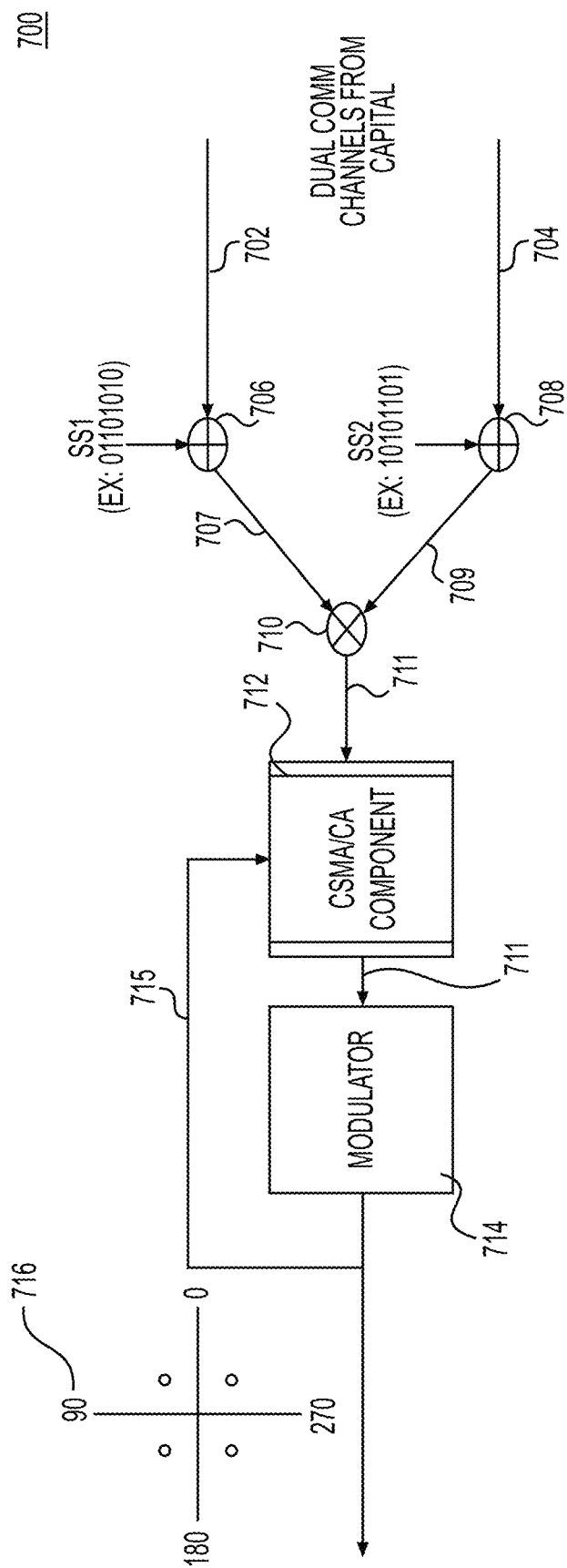
FIG. 7A is a diagram of an upstream transmission generation via a single stream protocol, according to aspects of this disclosure.
Figure 7B:
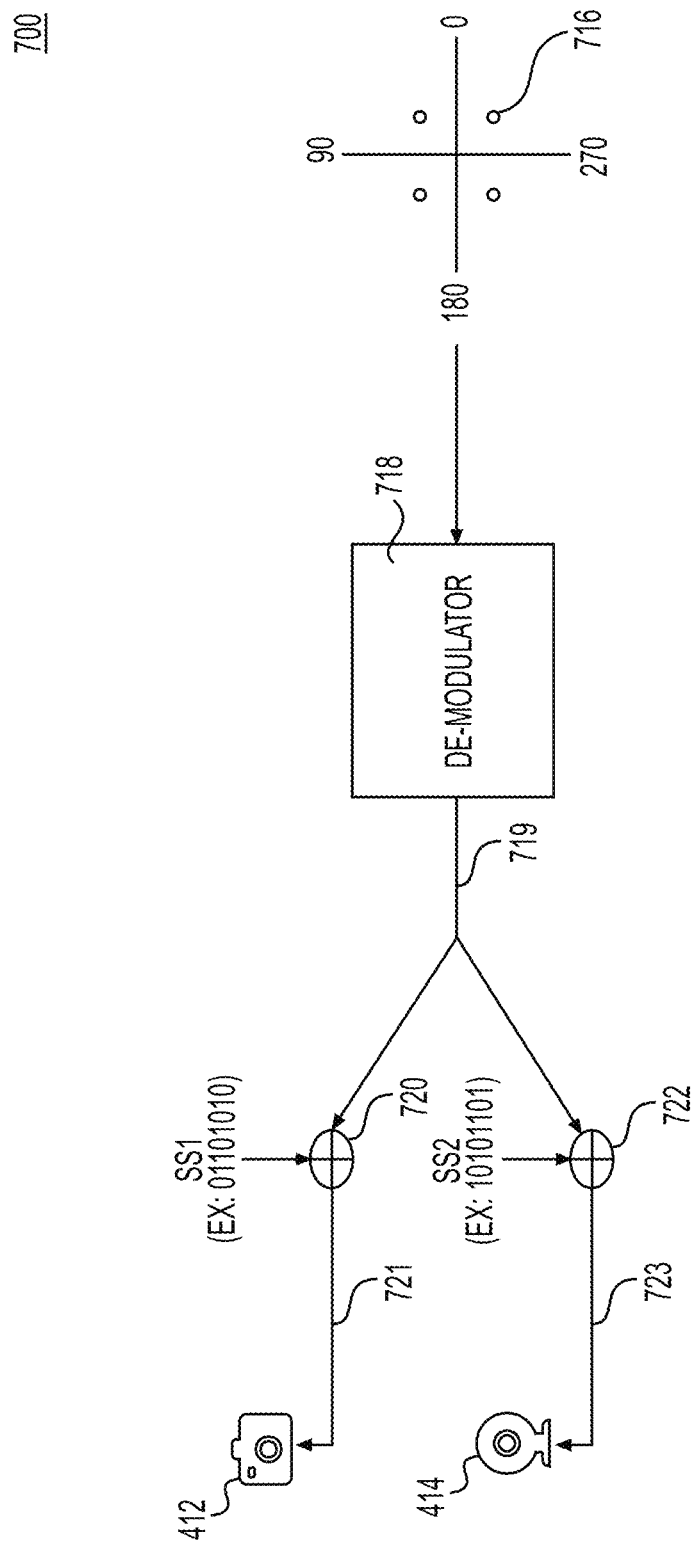
FIG. 7B is a diagram of an upstream transmission receipt via a single stream protocol, according to aspects of this disclosure.

Flowchart 600 of FIG. 6A provides a technique for generating modulated upstream data for upstream data communication. The techniques described in flowchart 600 may be performed at a controller, such as controller 170 of FIG. 1. Flowchart 650 of FIG. 6B provides a technique for providing first upstream data to a first sensing device and second upstream data to a second sensing device. The techniques described in flowchart 650 may be performed at a medical device, such as medical instrument 110 of FIG. 1. Additionally, various aspects of the techniques disclosed in FIGS. 6A and 6B are the same as or similar to those described in FIGS. 3A and 3B. Accordingly, for brevity, the overlapping disclosure is not re-produced in relation to FIGS. 6A and 6B. However, it will be understood that such disclosure, as provided for FIGS. 3A and 3B also applies to the techniques disclosed in FIGS. 6A and 6B. Additionally, FIGS. 7A and 7B show an example implementation of the techniques provided in FIGS. 6A and 6B.

At step 602 of FIG. 6A, as shown in diagram 700, a first upstream data 702 and a second upstream data 704 may be received at or generated in controller 700. The first upstream data 702 and the second upstream data 704 may each be from dual communication channels from controller 170. For example, the first upstream data 702 may be from a first communication channel configured to generate instructions for the first sensor 412 of FIG. 7B. Similarly, the second upstream data 704 may be from a second communication channel configured to generate instructions for the second sensor 414 of FIG. 7B. The first upstream data 702 and second upstream data 704 may require lower bandwidth than corresponding downlink data streams (e.g., data stream 413 and 415 of FIGS. 4A-4C).

At step 604, the first upstream data 702 may be spread (e.g., via application of the spreading logic 105 of FIG. 1) using a first orthogonal code. This spread operation may result in a first coded upstream data 707. As shown in FIG. 7A, the first upstream data 702 may be received at a first spreading component 706, and the first spreading component 706 may conduct the spreading operation using the first orthogonal code. The first spreading component 706 may be based in hardware, software, or firmware and may be configured to continuously receive the first upstream data 702.

Similarly, at step 606, the second upstream data 704 may be spread (e.g., via application of the spreading logic 105 of FIG. 1) using a second orthogonal code. The spread operation may result in a second coded upstream data 709. As shown in FIG. 7A, the second upstream data 704 may be received at a second spreading component 708, and the second spreading component 708 may conduct the spreading operation using the second orthogonal code. The second spreading component 708 may be based in hardware, software, or firmware and may be configured to continuously receive the second upstream data 704.

The first orthogonal code and the second orthogonal code each used to spread the first upstream data 702 and the second upstream data 704, respectively, may be sequences of binary digits (e.g., sequence 01101010 as the first orthogonal code and 10101101 as the second orthogonal code, as shown in FIG. 7A). The spreading operation at steps 604 and 606 of FIG. 6A may be implemented using a DSSS scheme and may multiply (XOR) the first upstream data 702 and the second upstream data 704 by the respective orthogonal code. According to an implementation, the first orthogonal code and the second orthogonal code may be the same as those applied in steps 306 and 308 of FIG. 3A during a downstream communication.

As disclosed herein, the bit rate of the orthogonal code may be higher than that of the respective upstream data such that a higher bandwidth of data is represented by the resulting coded upstream data. An example spreading operation is shown in FIG. 5, as described herein.

At step 608 of FIG. 6A, the first coded data upstream data 707 and the second coded upstream data 709 are combined into a combined upstream data 711 using a combination component 710. According to an implementation, the combination component 710 may be the same as or similar to combination component 420 of FIGS. 4A-4C.

At step 610, a carrier-sense multiple access with collision avoidance (CSMA/CA) protocol may be applied via a CSMA/CA component 712 to determine whether a transmission channel is idle to transmit the combined upstream data 711. The CSMA/CA component 712 may use a carrier sense media access technique to ensure that upstream data doesn't corrupt downstream data, and vice versa. The transmission channel may be the same wired or wireless channel discussed in reference to FIGS. 3A-3B and 4A-4C and was used to transmit and/or receive the modulated data stream 430. The CSMA/CA component 712 may operate such that when it receives a packet (e.g., combined upstream data 711) to be transmitted via the transmission channel, it determines whether the channel is clear such that no other transmission is processed at that time. The CSMA/CA component 712 may sample the channel via a sampling signal 715 to confirm that the channel is clear for transmission prior to the combined updated data 711 being modulated by modulator 714 and the modulated upstream data 716 being transmitted via modulator 714. For example, the CSMA/CA component 712 may determine if a modulated data stream 430 is being received by the controller 170 at the same time that a combined upstream data 711 is to be transmitted. If the channel is clear, then the combined upstream data 711 is transmitted via the CSMA/CA component 712 to the modulator 714. If the channel is not clear, the combined upstream data 711 is held for a period of time (e.g., a predetermined period of time, a dynamically determined period of time based on information blocking transmission, based on a randomly chosen period of time, etc.). Upon expiration of the period of time, the CSMA/CA component 712 again determines whether the transmission channel is clear. This determination is repeated until the channel is clear and the combined upstream data 711 is transmitted via the CSMA/CA component 712 to the modulator 714.

At step 612, the combined upstream data 711 is provided to a modulator 714 that modulates the combined upstream data 711 to generate a modulated upstream data 716. According to an implementation, the modulator 714 may be a simpler modulator than modulator 422 of FIGS. 4A-4C based on the type of data included in the combined upstream data 711 when compared to the combined data stream 421 of FIGS. 4A-4C. For example, the modulator 714 may be a phase-shift keying (PSK) modulator, a binary phase-shift keying (BPSK) modulator, a quadrature phase-shift keying (QPSK) modulator, a differential phase-shift keying (DPSK) modulator, an offset QPSK (OQPSK) modulator, or the like. According to another application, the modulator 714 may be the same as or similar to the modulator 422 of FIGS. 4A-4C (e.g., a QAM modulator (e.g., a QAM-16 modulator, a QAM-32 modulator, a QAM-64 modulator, a QAM-128 modulator, a QAM-256 modulator etc.), a frequency-shift keying (FSK) modulator, an orthogonal frequency-division multiplexing OFDM modulator, an application-specific integrated circuit ASIC modulator, etc.).

At step 614 of FIG. 6A, the combined upstream data 711 is transmitted via a single transmission channel. The single transmission channel may be the same transmission used for downlink transmission of the modulated data stream 430, in FIGS. 3A-3B and 4A-4C. As discussed herein, the single channel may be a wireless channel such that the modulated upstream data 716 is transmitted using a wireless component (e.g., a transmit antenna, a transceiver, etc.). According to another implementation, the single channel may be a single wired connection that provides the modulated upstream data 716 from the modulator 714 to a medical device component (e.g., umbilicus 118 of FIG. 1) via an electrical connector.

The modulated upstream data 716 may be provided to a medical device component (e.g., umbilicus 118 or handle 112 of FIG. 1) or other applicable component that enables the first upstream data 702 and the second upstream data 704 to be received at the first sensor 412 and second sensor 414, respectively, as further disclosed herein. As discussed herein, the modulated upstream data 716 may be transmitted via the same channel as the downlink transmission for the modulated data stream 430 to be received at the controller transmitting the modulated upstream data 716. As also discussed herein, a CSMA/CA or other applicable collision avoidance component such as multiple access with collision avoidance (MACA), or the like, may be applied to avoid corrupting the upstream or downstream data via a collision.

As shown in flowchart 650 of FIG. 6B, at step 652, the modulated upstream data 716 of FIGS. 7A and 7B may be received (e.g., by umbilicus 118 or other applicable component of medical system 100) via a single transmission channel, as discussed herein. As an example, the modulated upstream data 716 may be received by a receiving antenna or transceiver located at the umbilicus 118 or other component of medical system 100.

FIG. 7B shows an implementation for demodulating the modulated upstream data 716 to provide applicable upstream data (e.g., first upstream data 702 and second upstream data 704) to the first sensor 412 and second sensor 414. The first sensor 412 and the second sensor 414 are the same sensors as those shown in FIGS. 4A-4C. However, it will be understood that the techniques described in FIGS. 6A-6B and 7A-7B may be implemented for sensors different than the same first sensor 412 and second sensor 414 of FIGS. 4A-4C.

As shown in FIG. 7B, the modulated upstream data 716 may be received at a de-modulator 718 that may de-modulate the modulated upstream data 716 to extract the combined upstream data 719. The de-modulator 718 may be a phase-shift keying (PSK) de-modulator, a binary phase-shift keying (BPSK) de-modulator, a quadrature phase-shift keying (QPSK) de-modulator, a differential phase-shift keying (DPSK) de-modulator, an offset QPSK (OQPSK) de-modulator, or the like. Alternatively, the demodulator may be a QAM de-modulator (e.g., a QAM-16 de-modulator, a QAM-32 de-modulator, a QAM-64 de-modulator, a QAM-128 de-modulator, a QAM-256 de-modulator etc.), an FSK de-modulator, an OFDM de-modulator, ASIC de-modulator, etc. The de-modulator 718 may be selected based on the modulator 714 such that the demodulation conducted at step 654 of FIG. 6B corresponds to the modulation conducted at step 612 of FIG. 6A.

De-modulating the modulated upstream data 716 may provide the combined upstream data 719 that corresponds to the combined upstream data 711. According to an implementation, the combined upstream data 719 may be identical or approximately identical to the combined upstream data 711. According to another implementation, the combined upstream data 719 may be a derivation or augmented version of the combined upstream data 711. The combined upstream data 719 may be provided such that it enables the extraction of the upstream data 721 and 723, as further disclosed herein.

At step 656, the first orthogonal code used at step 606 may be applied (e.g., XOR multiplication) to the combined upstream data 719. The first orthogonal code may be applied by a first extraction component 720. According to an implementation, the first extraction component 720 may be the same as or similar to the first spreading component 706. In the example provided in FIG. 7A, the first orthogonal code 01101010 may be XORed with the combined upstream data 719 to extract the first upstream data 721. According to an implementation, the first upstream data 721 may be identical or approximately identical to the first upstream data 702. According to another implementation, the first upstream data 721 may be a derivation or augmented version of the first upstream data 702. The first upstream data 721 may be extracted such that it serves the same practical function as if the first upstream data 702 was received at the first sensor 412.

Similarly, at step 658, the second orthogonal code used at step 608 may be applied (e.g., XOR multiplication) to the combined upstream data 719. The second orthogonal code may be applied by a second extraction component 722. According to an implementation, the second extraction component 722 may be the same as or similar to the second spreading component 708. In the example provided in FIGS. 7A, the second orthogonal code 10101101 may be XORed with the combined upstream data 719 to extract the second upstream data 723. According to an implementation, the second upstream data 723 may be identical or approximately identical to the second upstream data 704. According to another implementation, the second upstream data 723 may be a derivation or augmented version of the second upstream data 723. The second upstream data 723 may be extracted such that it serves the same practical function as if the second upstream data 704 was received at second sensor 414.

At step 660 of FIG. 6B, the first upstream data 721 may be provided to the first sensor 412, and the second upstream data 723 may be provided to the second sensor 414. The first sensor 412 may take an action (e.g., sense, stop sensing, physically move, change a property, etc.) based on the first upstream data 721, and the second sensor 414 may take an action based on the second upstream data 723.

According to implementations, any of the disclosed systems, methods, and/or devices may be executed by or implemented by a computing system consistent with or similar to the descriptions herein. Although not required, aspects of this disclosure are described in the context of computer-executable instructions, such as routines executed by a data processing device, e.g., a server computer, wireless device, and/or personal computer. Those skilled in the relevant art will appreciate that aspects of this disclosure can be practiced with other communications, data processing, or computer system configurations, including: Internet appliances, hand-held devices (including personal digital assistants ("PDAs")), wearable computers, all manner of cellular or mobile phones (including Voice over IP ("VoIP") phones), dumb terminals, media players, gaming devices, virtual reality devices, multi-processor systems, microprocessor-based or programmable consumer electronics, set-top boxes, network PCs, mini-computers, mainframe computers, and the like. Indeed, the terms "computer," "computing device," and the like, are generally used interchangeably herein, and refer to any of the above devices and systems, as well as any data processor.

Aspects of this disclosure may be embodied in a special purpose computer and/or data processor that is specifically programmed, configured, and/or constructed to perform one or more of the computer-executable instructions explained in detail herein. While aspects of this disclosure, such as certain functions, are described as being performed exclusively on a single device, this disclosure may also be practiced in distributed environments where functions or modules are shared among disparate processing devices, which are linked through a communications network, such as a Local Area Network ("LAN"), Wide Area Network ("WAN"), and/or the Internet. Similarly, techniques presented herein as involving multiple devices may be implemented in a single device. In a distributed computing environment, program modules may be located in both local and/or remote memory storage devices.

Aspects of this disclosure may be stored and/or distributed on non-transitory computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data under aspects of this disclosure may be distributed over the Internet and/or over other networks (including wireless networks), on a propagated signal on a propagation medium (e.g., an electromagnetic wave(s), a sound wave, etc.) over a period of time, and/or they may be provided on any analog or digital network (packet switched, circuit switched, or other scheme).

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

It should be understood that one or more of the aspects of any of the medical devices described herein may be using in combination with any other medical device known in the art, such as medical imaging systems or other scopes such as colonoscopes, bronchoscopes, ureteroscopes, duodenoscopes, etc., or other types of imagers.

It will be apparent to those skilled in the art that various modifications and variations may be made in the disclosed devices and methods without departing from the scope of the disclosure. It should be appreciated that the disclosed devices may include various suitable computer systems and/or computing units incorporating a plurality of hardware components, such as, for example, a processor and non-transitory computer-readable medium, that allow the devices to perform one or more operations during a procedure in accordance with those described herein. Other aspects of the disclosure will be apparent to those skilled in the art from consideration of the specification and practice of the features disclosed herein. It is intended that the specification and examples be considered as exemplary only.

We claim:

1. A medical system comprising:
a first sensor configured to generate a first data stream;
a second sensor configured to generate a second data stream;
at least one processor;
at least one non-transitory computer readable medium storing instructions that, when executed by the at least one processor, cause the at least one processor to:
receive the first data stream and the second data stream;
manipulate the first data stream and the second data stream to generate a single data stream; and
transmit the single data stream via a single transmission channel; and
a controller configured to:
receive the single data stream for processing via the single transmission channel; and
prevent any other transmission via the single transmission channel as the single data stream is being received from the at least one processor via the single transmission channel.

2. The medical system of claim 1, wherein, to manipulate the first data stream and the second data stream to generate the single data stream, the instructions cause the at least one processor to:
spread the first data stream and the second data stream;
combine the spread first data stream and the spread second data stream to generate a combined data stream; and modulate the combined data stream to generate the single data stream.

3. The medical system of claim 2, wherein, to spread the first data stream and the second data stream, the instructions cause the at least one processor to:
spread the first data stream using a first code to generate a first coded data stream; and
spread the second data stream using a second code to generate a second coded data stream.

4. The medical system of claim 3, wherein the controller is further configured to:
de-modulate the single data stream to extract the combined data stream;
apply the first code to extract the first data stream from the combined data stream;
apply the second code to extract the second data stream from the combined data stream; and
process the first data stream and the second data stream.

5. The medical system of claim 2, wherein the combined data stream is modulated using a Quadrature Amplitude Modulation (QAM) modulator.

6. The medical system of claim 1, wherein the single transmission channel is one of a copper channel, a fiber channel, or air.

7. The medical system of claim 1, wherein, to prevent any other transmission via the single transmission channel as the single data stream is being received, the controller is configured to:
prior to transmitting any uplink data streams from the controller to the at least one processor via the single transmission channel, determine whether the single transmission channel is idle; and
transmit the uplink data streams via the single transmission channel only upon a determination that the single transmission channel is idle.

8. The medical system of claim 7, wherein the controller is configured to apply a carrier-sense multiple access with collision avoidance (CSMA/CA) protocol to determine whether the single transmission channel is idle.

9. The medical system of claim 1, wherein at least one of the first sensor or the second sensor is an image sensor of a medical device.

10. The medical system of claim 1, wherein each of the first sensor and the second sensor is an image sensor of a medical device.

11. The medical system of claim 1, wherein the first sensor is a first image sensor of a first medical device, and the second sensor is a second image sensor of one of the first medical device or a second medical device used with the first medical device to perform a medical procedure.

12. A medical system comprising:
a plurality of sensors configured to generate a plurality of data streams;
a medical instrument communicatively coupled to the plurality of sensors, and comprising:
at least one processor; and
at least one non-transitory computer readable medium storing instructions that, when executed by the at least one processor, cause the at least one processor to:
receive the plurality of data streams;
spread, combine, and modulate the plurality of data streams to generate a single data stream; and
transmit the single data stream via a single transmission channel; and
a controller communicatively coupled to the medical instrument, and configured to:
receive the single data stream via the single transmission channel;
prevent any other transmission via the single transmission channel as the single data stream is being received from the at least one processor via the single transmission channel in order to avoid corrupting the single data stream; and
de-modulate and extract the plurality of data streams from the single data stream.

13. The medical system of claim 12, wherein the controller is configured to apply a carrier-sense multiple access with collision avoidance (CSMA/CA) protocol to prevent any other transmission via the single transmission channel as the single data stream is being received from the at least one processor via the single transmission channel.

14. The medical system of claim 13, wherein the single data stream is a downlink data stream, and to apply the CSMA/CA protocol, the controller is configured to:
determine, by applying the CSMA/CA protocol, whether the single transmission channel is available prior to transmitting an uplink data stream generated by the controller to the at least one processor.

15. The medical system of claim 14, wherein, as the single data stream is being received from the at least one processor via the single transmission channel, the controller determines the single transmission channel is unavailable, and holds the uplink data stream for a period of time until at least the determination is repeated and the single transmission channel is determined to be available.

16. The medical system of claim 13, wherein the medical instrument includes one or both of the plurality of sensors.

17. The medical system of claim 12, wherein, to spread, combine, and modulate the plurality of data streams to generate the single data stream, the instructions cause the at least one processor to:
spread each of the plurality of data streams using a code to generate a plurality of coded data streams;
combine the plurality of coded data streams to generate a combined data stream; and
modulate the combined data stream to generate the single data stream.

18. The medical system of claim 17, wherein, to de-modulate and extract the plurality of data streams for processing, the controller is further configured to:
de-modulate the single data stream to extract the combined data stream;
apply the code to extract each of the plurality of data streams from the combined data stream; and
process the plurality of data streams.

19. A method implemented by a controller communicatively coupled to a medical instrument, the method comprising:
generating, by the controller, an uplink data stream for transmission to the medical instrument via a single transmission channel;
receiving, from the medical instrument, a downlink data stream via the single transmission channel, wherein the downlink data stream is a single data stream comprised of a plurality of data streams generated by a plurality of sensors associated with the medical instrument and manipulated by a data processing device of the medical instrument to generate the single data stream;
prior to the transmission of the uplink data stream, determining the single transmission channel is unavailable based on the receiving of the downlink data stream via the single transmission channel; and holding the transmission of the uplink data stream for a period of time until at least the determination is repeated and the single transmission channel is determined to be available to prevent the uplink data stream from corrupting the downlink data stream.

20. The method of claim 19, wherein determining the single transmission channel is unavailable comprises:
transmitting a sampling signal via the single transmission channel, wherein a response to the sampling signal indicates a transmission is currently occurring on the single transmission channel.

* * * * *